United States Patent [19]

Dasilva Jardine

[11] Patent Number: 5,300,668
[45] Date of Patent: Apr. 5, 1994

[54] CERTAIN ESTERS OF 1-(4-X-METHYLPHENYL)CYCLOPENT-3-ENE-1-CARBOXYLIC ACID, WHEREIN X IS A TRIALKYLSILYLOXY, BROMO OR HYDROXY GROUP, AS INTERMEDIATES

[75] Inventor: Paul A. Dasilva Jardine, Mystic, Conn.

[73] Assignee: Pfizer Inc, New York, N.Y.

[21] Appl. No.: 43,959

[22] Filed: Mar. 10, 1993

[51] Int. Cl.$^5$ .................... C07C 62/32; C07C 61/20; C07F 7/18
[52] U.S. Cl. .................... 556/441; 560/59; 560/102; 546/118
[58] Field of Search .................... 560/59, 102; 556/441

[56] References Cited

U.S. PATENT DOCUMENTS 2,573,015 10/1951 Häfliger et al. .................... 562/492

FOREIGN PATENT DOCUMENTS

| 0485929 | 5/1992 | European Pat. Off. |
| 0513533 | 11/1992 | European Pat. Off. |
| 9111909 | 8/1991 | World Int. Prop. O. |
| 9111999 | 8/1991 | World Int. Prop. O. |
| 9112001 | 8/1991 | World Int. Prop. O. |

*Primary Examiner*—Bernard Dentz
*Attorney, Agent, or Firm*—Peter C. Richardson; Gregg C. Benson; D. Stuart McFarlin

[57] ABSTRACT

1-[4'-(2''-Ethyl-5'',7''-dimethylimidazo[4,5-b]pyridin-3-yl)methylphenyl]cyclopent-3-ene-1-carboxylic acid and its pharmaceutically acceptable salts inhibit angiotensin II in mammals and are useful in treating conditions such as hypertension, congestive heart failure and glaucoma and as the active ingredient in pharmaceutical compositions for treating such conditions.

6 Claims, No Drawings

CERTAIN ESTERS OF 1-(4-X-METHYLPHENYL)CYCLOPENT-3-ENE-1-CARBOXYLIC ACID, WHEREIN X IS A TRIALKYLSILYLOXY, BROMO OR HYDROXY GROUP, AS INTERMEDIATES

BACKGROUND OF THE INVENTION

This invention relates to a certain benzylimidazopyridine which has utility as a regulator of the action of angiotensin II (AII), mediated by the AII receptor, in mammals, including humans, and accordingly, is useful in the treatment of hypertension, congestive heart failure, glaucoma and other conditions for which the action of AII if implicated. This invention relates also to pharmaceutical compositions containing this compound and to methods of inhibiting AII in mammals by administration of said compound.

The renin-angiotensin system (RAS) acts as a crucial regulatory mechanism in the control of homeostasis and fluid/electrolyte balance in mammals, including humans. Consequently, RAS activity has a direct influence on blood pressure and has been found to play an important role in congestive heart failure and in the development and maintenance of hypertension. Additionally, AII activity has been implicated in the development of elevated intraocular pressure, for example, as caused by glaucoma. AII, an octapeptide hormone produced via the cleavage of angiotensin I (AI) by angiotensin converting enzyme (ACE), is a potent and direct arterial vasoconstrictor, thereby effecting an increase in vascular resistance and blood pressure. AII is also known to stimulate the release of aldosterone, resulting in vascular congestion and hypertension by promoting the retention of sodium and fluids. The present invention concerns regulation of the actions of AII which are mediated by the AII receptor.

Various benzylimidazole-derived compounds have been described as AII antagonists. For example, see P. C. Wong et al., *Hypertension*, 15 (5), 459–468 (1990), U.S. Pat. No. 4,207,324, EP 403158, EP 425211 A1 and WO 91/11999. Additionally, compounds of the same nature as that of the present invention are disclosed generically, but not specifically, in EP 513533 A2.

SUMMARY OF THE INVENTION

The present invention relates to a compound having the formula

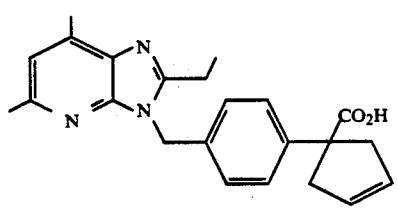

namely, 1-[4'-(2''-ethyl-5'',7''-dimethylimidazo[4,5-b]pyridin-3-yl)methylphenyl]cyclopent-3-ene-1-carboxylic acid, and its pharmaceutically acceptable salts.

This invention also concerns pharmaceutical compositions comprising said compound, methods of making and using said compound and intermediates in the preparation of said compound. The novel intermediates of the invention include the $C_1$ to $C_4$ alkyl and halosubstituted $C_2$ to $C_4$ alkyl esters of the compound (see Example 1, Steps 5 and 3A) and its precursors (Example 1, Steps 2 to 4). This invention relates also to pharmaceutically acceptable compositions of this novel compound in combination with other antihypertensive and cardiotonic agents, including beta blockers, diuretics, angiotensin converting enzyme inhibitors, calcium channel blockers, atrial natriuretic factor peptidase inhibitors, renin inhibitors and digitalis. This invention further relates to the use of this novel compound in the treatment of central nervous system disorders such as, for example, cognitive dysfunction including Alzheimer's disease, amnesia and senile dementia, depression, anxiety and dysphoria. Furthermore, it may be used to treat glaucoma and diabetic complications such as diabetic renal disease.

DETAILED DESCRIPTION OF THE INVENTION

As used herein, the following definitions are used.

"Halo" means radicals derived from the elements fluorine, chlorine, bromine and iodine.

"Alkyl" means straight or branched saturated hydrocarbon radicals, for example, methyl, ethyl, n-propyl, isopropyl, n-butyl, isobutyl and t-butyl.

The compound of the present invention may be prepared by a number of routes, including the following.

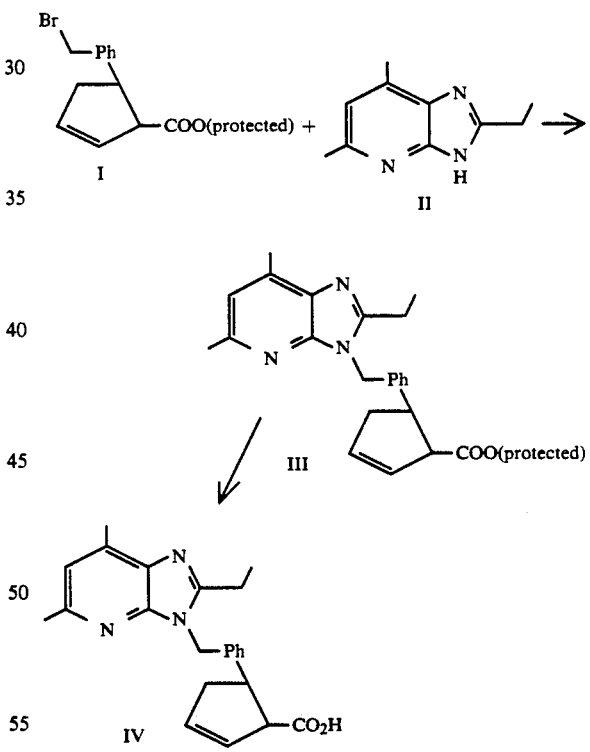

In the reaction scheme depicted above, the compound of the present invention is prepared by alkylating an imidazopyridine (II, prepared, for example, by the methods described in EP 400974 A2) with a bromide (I, prepared by standard methods, as illustrated in the example below) in the presence of a basic agent. Suitable bases include, for example, sodium hydride, potassium tert-butoxide and potassium carbonate. The reaction preferably takes place in a reaction-inert solvent such as, for example, dimethylformamide (DMF), tetrahydrofuran (THF) and/or acetone. The desired protected compound (III) is purified by standard methods, for example, chromatography and/or recrystallization. The carboxyl functionality is then deprotected by standard methods, for example, with an aqueous base such as sodium or lithium hydroxide in methanol or THF, to afford the desired final product (IV), which can be further purified by standard methods such as chromatography and/or recrystallization.

The compound of the present invention is readily adapted to clinical use as a modulator of AII action at the AII receptor. The ability of the compound to modulate AII action was determined by an in vitro AII rat liver binding assay which measures its ability to displace $^{125}I$ sarcosine-1, isoleucine-8, angiotensin II (SARILE AII, obtained from New England Nuclear) from rat liver AII receptors. For this assay, the following materials are used.

Homogenation buffer (10 mM Tris, 0.2M sucrose, 1.0 mM EDTA), prepared using 1.21 g Tris base, 6.84 g sucrose and 336 mg EDTA in 1000 ml water, adjusted to pH 7.4 using HCl.

Buffer A (50 mM Tris, 5 mM $MgCl_2$), prepared using 6.05 g Tris base and 1.02 g $MgCl_2.6H_2O$ in 1000 ml water.

Assay buffer, prepared using 200 ml Buffer A and 0.5 g BSA.

Male Sprague-Dawley rats are sacrificed by decapitation and the livers are removed quickly and placed in ice cold homogenation buffer (all the following procedures are performed at 4° C.). The liver is minced with scissors and homogenized in a chilled ground glass homogenizer at approximately 10 ml buffer/1 g liver (wet weight). The homogenate is centrifuged at 3000 g (5000 rpm, SM24 rotor) for 10 minutes, then the supernatant is centrifuged at 10,000 g for 13 minutes. The resulting supernatant is then centrifuged at 100,000 g for one hour. The pellet is resuspended in buffer A to an approximate concentration of 1 ml protein/ml. A BioRad protein assay using Coomassie blue dye is then run. The membrane preparation is aliquoted, frozen and stored at $-20°$ C. On the day of the assay, the preparation is diluted with assay buffer to a final concentration of 600 $\mu g$/ml or with buffer A to a final concentration of 200 $\mu g$/ml. Due to the fact that the compound of the invention may bind to proteins, the use of BSA may interfere with some tests. Accordingly, the assay may be run with or without BSA; the differences are identified below.

The compound being tested is made up to an initial concentration of 2 mM in 100% DMSO. Dilutions are then made using 10% DMSO in assay buffer or buffer A. Radiolabelled (hot) SARILE AII is made up at 0.5 nM concentration in assay buffer or 1.0 nM concentration in buffer A. Non-radiolabelled (cold) SARILE AII is made up at 20 $\mu M$ in 10% DMSO in assay buffer or buffer A for non-specific binding. Using microtitre plates, each incubate receives: 50 $\mu l$ hot SARILE AII; 50 $\mu l$ membrane preparation; and 100 $\mu l$ buffer (total), cold SARILE AII (nonspecific binding) or compound to be tested. Each plate consists of the following in triplicate: total binding; nonspecific binding; and varying concentration of compound. Plates are incubated at room temperature for 40 minutes for assays containing BSA or for 120 minutes for assays without BSA, on a rocker plate at high speed. Plates are then aspirated using an Inotech cell harvester. The filters are cut, placed in test tubes and counted on a Gamma Counter. The mean for all triplicate points are calculated and total specific binding is calculated by subtracting nonspecific counts from total counts. Binding in the presence of compound (COUNTS) is calculated by subtracting nonspecific counts from counts in the presence of compound. Percent binding of SARILE AII in the presence of compound is calculated by dividing COUNTS by total specific counts. Percent inhibition is (1-percent binding)*100. $IC_{50}$ values (concentration of compound which inhibits binding by 50%) is read from a plot of percent inhibition (linear scale) versus compound concentration (log scale). The compound of the present invention was found to have $IC_{50}$ values of less than $10^{-7}M$.

The ability of the compounds of the invention to lower blood pressure in mammals was determined by the following in vivo protocol. Sprague-Dawley rats are placed on a low sodium diet (Purina Labs, 0.07% sodium) for 15 days. On days 11 and 13 of this period, the rats are given furosemide (Lasix, 8 mg/kg, i.m.). On day 13, the animals are anesthetized with a pentobarbital-chloral hydrate mixture (30 mg/kg pentobarbital sodium and 10 mg/kg chloral hydrate, i.p.) and the carotid artery and jugular vein are cannulated using PE50 tubing (Clay-Adams). After a 24 hour recovery period, the animals are injected on day 14 with Lasix (10 mg/kg, i.m.) and are placed in plexiglass chambers for blood pressure recording. After dosing rats by either the oral or parenteral routes with the compound being tested, blood pressure is monitored for 5 hours and is displayed on a polygraph. When possible, blood pressure is also checked after 24 hours. According to this protocol, the compound of the invention is effective in lowering mean arterial pressure at oral dosages from about 0.1 mg/kg to about 30 mg/kg, and at parenteral dosages from about 0.01 mg/kg to about 10 mg/kg, with a duration of action of greater than 24 hours.

Also within the scope of this invention are the pharmaceutically acceptable salts of the compound of this invention. The pharmaceutically acceptable acid salts are those formed from acids which form non-toxic acid salts, for example, hydrochloride, hydrobromide, sulfate, bisulfate, phosphate, acid phosphate, acetate, citrate, fumarate, gluconate, lactate, maleate, succinate, tartrate, methanesulfonate, benzenesulfonate, toluenesulfonate and formate salts. Pharmaceutically acceptable cationic salts include those non-toxic salts based on alkali and alkaline earth metals, for example, sodium, lithium, potassium, calcium and magnesium, as well as non-toxic ammonium, quaternary ammonium and amine cations, for example, ammonium, tetramethylammonium, methylamine, dimethylamine, trimethylamine, ethylamine, diethylamine and triethylamine.

Such salts are formed by methods well known to those skilled in the art. The pharmaceutically acceptable salts of the novel compound of the present invention are readily prepared by contacting said compound with a stoichiometric amount of, in the case of a non-toxic cation, an appropriate metal hydroxide, alkoxide or amine either aqueous solution or a suitable organic solvent. In the case of non-toxic acid salt, an appropriate mineral or organic acid in either aqueous solution or a suitable organic solvent can be used. The salt may then be obtained by precipitation or by evaporation of the solvent.

For treatment of the various conditions described above, the compound of the invention and its pharmaceutically acceptable salts can be administered to the patient either alone or, preferably, in combination with pharmaceutically acceptable carriers or diluents in a pharmaceutical composition, according to standard pharmaceutical practice. The compound can be administered via a variety of conventional routes of administration including orally, parenterally and by inhalation. When the compound is administered orally, the dose range will generally be from about 0.1 to about 50 mg/kg/day, based on the body weight of the subject to be treated, preferably from about 1 to about 10 mg/kg/day in single or divided doses. If parenteral administration is desired, then an effective dose will generally be from about 0.01 to about 10 mg/kg/day. In some instances it may be necessary to use dosages outside these limits, since the dosage will necessarily vary according to the age, weight and response of the individual patient as well as the severity of the patient's symptoms.

For oral administration, the compound of the invention and its pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile injectable solution of the active ingredient is usually prepared, and the pH of the solution should be suitably adjusted and buffered. For intravenous use, the total concentration of solute should be controlled to make the preparation isotonic.

EXAMPLES

The present invention is illustrated by the following examples. Proton nuclear magnetic resonance ($^1$H NMR) spectra were measured at 300 MHz unless otherwise indicated and peak positions are expressed in parts per million (ppm) downfield from tetramethylsilane. The peak shapes are denoted as follows: s, singlet; d, doublet; t triplet; q, quartet; m, multiplet; br, broad.

EXAMPLE 1

1-[4'-(2''-ethyl-5'',7''-dimethylimidazo[4,5-b]pyridin-3-yl)methylphenyl]cyclopent-3-ene-1-carboxylic acid Step 1, methyl 4-t-butyldimethylsilyloxymethylphenylacetate To a solution of methyl p-hydroxymethylphenylacetate (3.30 g, 18.3 mmol, prepared according to the method of G. Biagi et al., *E. Ed. Farmaco.*, 43, 597 (1988)) in 6.6 ml DMF was added TBDMS-Cl (3.31 g, 22.0 mmol) and imidazole (3.12 g, 45.8 mmol), and the resulting solution was stirred at ambient temperature for 18 hours. The mixture was poured into 100 ml H$_2$O and extracted (EtOAc, 4×50 ml). The combined extracts were dried (MgSO$_4$), filtered and concentrated. The crude material was chromatographed (EtOAc:hexane, 5:95) to afford the title compound (5.0 g, 92% yield) as an oil.

$^1$H NMR (CDCl$_3$) δ 0.09 (s, 6H), 1.94 (s, 9H), 3.60 (s, 2H), 3.67 (s, 3H), 4.70 (s, 2H), 7.23 (m, 4H).

Step 2, methyl 1-(4'-t-butyldimethylsilyloxymethylphenyl)cyclopent-3-ene-1-carboxylate To a solution of the product of Step 1, above, (1.0 g, 3.4 mmol) in 10 ml THF at −20° C. was added a 1M solution of potassium t-butoxide in THF (3.73 ml, 3.73 mmol) over 15 minutes. After 30 minutes at −20° C., cis-1,4-dichlorobut-2-ene (0.393 ml, 3.73 mmol) was added dropwise and the reaction was warmed to room temperature. After 20 minutes the reaction was cooled to −20° C. and treated with potassium t-butoxide in THF (3.73 ml, 3.73 mmol). The reaction was allowed to warm to room temperature, then was heated at 50° C. for 30 minutes and quenched with saturated ammonium chloride solution. The solvents were removed in vacuo and the residue was taken up in ethyl acetate and washed with water. The organic layer was washed with saturated sodium chloride solution and dried over magnesium sulfate. After filtration, evaporation and gravity silica gel chromatography (SGC) with 2% ethyl acetate in petroleum ether as eluant, a mixture of the title compound and methyl 1-(4'-t-butyldimethylsilyloxymethylphenyl)-2-vinylcyclopropane-1-carboxylate (7:1 ratio, total 708 mg) was obtained as an oil. Since the two compounds were inseparable, the mixture was taken on.

$^1$H NMR (CDCl$_3$) δ 0.09 (s, 6H), 0.9 (s, 9H), 2.75 (d, 2H), 3.40 (d, 2H), 3.65 (s, 3H), 4.72 (s, 2H), 5.78 (s, 2H), 7.25 (m, 4H).

Step 3, methyl 1-(4'-hydroxymethylphenyl)cyclopent-3-ene-1-carboxylate

To a solution of the title compound of Step 2, above, (1.8 g, 5.23 mmol) in 25 ml THF was added n-Bu$_4$NF (1.5 g, 5.75 mmol), and the resulting solution was stirred at ambient temperature for 3 hours. The mixture was poured into 50 ml 1N HCl and extracted (EtOAc, 4×30 ml). The combined extracts were dried over MgSO$_4$, filtered and concentrated to yield 1.51 g of the title compound as an oil which was used crude in the next step.

$^1$H NMR (CDCl$_3$) δ 2.74 (d, 2H), 3.40 (d, 2H) 3.66 (s, 3H), 4.65 (s, 2H), 5.76 (s, 2H), 7.26 (m, 4H).

Step 4, methyl 1-(4'-bromomethylphenyl)cyclopent-3-ene-1-carboxylate

To a solution of triphenylphosphine (8.03 g, 30.6 mmol) in 100 ml CH$_2$Cl$_2$ at 0° C. was added dropwise bromine (1.45 ml, 28.1 mmol). After 15 minutes at 0° C. a white precipitate formed and a solution of the product of Step 3, above, (5.93 g, 25.5 mmol) in 30 ml CH$_2$Cl$_2$ was added dropwise. After 1 hour the solvent was removed in vacuo and the residue was taken up in ether to precipitate the triphenylphosphine oxide formed in the reaction. After filtration, evaporation and SGC (5% EtOAc-hexanes) the title compound (5 g) was obtained as a colorless oil which crystallized on standing.

$^1$H NMR (CDCl$_3$) δ 2.73 (d, 2H), 3.62 (s, 3H), 4.48 (s, 2H), 5.77 (s, 2H), 7.20 (m, 4H).

Step 5, methyl 1-[4'-(2''-ethyl-5'',7''-dimethylimidazo[4,5-b]pyridin-3-yl)methylphenyl]cyclopent-3-ene-1-carboxylate To a suspension of sodium hydride (0.885 g, 22.1 mmol) in 50 ml of DMF at 0° C. was added a solution of 2-ethyl-5,7-dimethyl-3H-imidazo[4,5-b]pyridine (3.57 g, 20 mmol, prepared from 2-amino-4,6-dimethylpyridine by nitration, hydrogenolysis to the diamine and condensation with propionic acid and polyphosphoric acid, as described in EP 400974 A2) in 10 ml of DMF dropwise and the reaction mixture was warmed to room temperature. After 20 minutes the reaction was cooled to 0° C. and a solution of the product of Step 4, above, (5 g, 17 mmol) in 10 ml of DMF was added dropwise. The reaction was then allowed to warm to room temperature and stirred overnight then the DMF was removed in vacuo. The residue was taken up in water and extracted three times with ethyl acetate. The combined organics were washed with saturated sodium chloride solution, dried with MgSO₄, filtered, evaporated and chromatographed on silica gel with a gradient elution from 5:1 hexanes:ethyl acetate to 1:1 hexanes:ethyl acetate to yield 5.8 g of the title compound as a pale yellow oil.

$^1$H NMR (CDCl₃) δ 1.3 (t, 3H), 2.59 (s, 3H), 2.62 (s, 3H), 2.7 (d, 2H), 2.8 (q, 2H), 3.4 (d, 2H), 3.63 (s, 3H), 5.4 (s, 2H), 5.72 (s, 2H), 6.9 (s, 1H), 7.1 (d, 2H), 7.28 (d, 2H).

Step 6,
1-[4'-(2"-ethyl-5",7"-dimethylimidazo[4,5-b]pyridin-3-yl)methylphenyl]cyclopent-3-ene-1-carboxylic acid A solution of the product of Step 5, above (5.76 g, 14.9 mmol) and lithium hydroxide monohydrate (6.23 g, 148 mmol) in 148 ml of methanol and 148 ml of water was heated at reflux for 2 hours. The reaction was then concentrated in vacuo, the residue was taken up in water and the pH was adjusted to 4 with concentrated HCl when the title compound precipitated as a colorless solid which was filtered off, dried in vacuo and recrystallized first from ethyl acetate/methanol, then from methanol to yield 1.9 g of title compound which was contaminated with 2.5% of 1-[4'-(2"-ethyl-5",7"-dimethylimidazo[4,5-b]pyridin-3-yl)methylphenyl]-2-vinylcyclopropane-1-carboxylic acid. Another recrystallization from methanol yielded 1.5 g of title compound, mp 232°–233° C., now about 98.3% pure, as determined by reverse-phase HPLC using a C-18 Beckman 25 cm long column and 30% pH 2.3 phosphate buffer in acetonitrile as eluant.

$^1$H NMR (DMSO-d₆) δ 1.24 (t, 3H), 2.5 (s, 6H), 2.6 (d, 2H), 2.8 (q, 2H), 3.3 (d, 2H), 5.4 (s, 2H), 5.75 (s, 2H), 6.95 (s, 1H), 7.09 (d, 2H), 7.3 (d, 2H).

Alternatively, and preferably, the compound of Example 1 can be prepared via the following method.

Step 1A,
4'-(2"-ethyl-5",7"-dimethylimidazo[4,5-b]pyridin-3-yl)methylphenylacetic acid A solution of 4-(bromomethyl)phenylacetic acid (24.53 g, 107 mmol) in 60 ml DMF was added slowly to a suspension of sodium hydride (4.29 g, 60% dispersion in oil, 107 mmol) in 240 ml of DMF at −25° C. and the reaction mixture was stirred at −20° C. for 30 minutes. Meanwhile, 2-ethyl-5,7-dimethylimidazo[4,5-b]pyridine (15 g, 85.7 mmol) was added as a solid to a suspension of sodium hydride (3.43 g, 60% dispersion in oil, 85.7 mmol) in 180 ml of DMF at −10° C. and the reaction was allowed to warm to room temperature over 30 minutes, then was cooled to −20° C. and treated via cannula with the solution of the sodium salt of 4-(bromomethyl)phenylacetic acid in DMF prepared above. After the addition was complete, the reaction mixture was cooled in a ice bath at −10° C. and was allowed to warm to room temperature overnight. The DMF was removed in vacuo and the residue was taken up in water and extracted with ethyl acetate. The aqueous layer was adjusted to pH 4 with concentrated hydrochloric acid an was extracted twice with ethyl acetate. The combined organic layers were washed with saturated sodium chloride and dried over magnesium sulfate. Concentration afforded the title compound (18 g) as a pale yellow solid which was used without further purification.

$^1$H NMR (CD₃OD) δ 1.25 (t, 3H), 2.55 (s, 3H), 2.6 (s, 3H), 2.8 (q, 2H), 3.6 (s, 2H), 5.5 (s, 2H), 6.9–7.3 (m, 5H).

Step 2A, methyl
4'-(2"-ethyl-5",7"-dimethylimidazo[4,5-b]pyridin-3-yl)methylphenylacetate The product of Step 1A, above (56 g), was dissolved in 1 L methanol at room temperature and was treated with 11 ml concentrated sulfuric acid and the reaction mixture was stirred at room temperature overnight. The reaction was quenched with saturated sodium bicarbonate solution and concentrated. The residue was taken up in water and extracted three times with ethyl acetate. The combined organic layers were washed with saturated sodium chloride and dried over magnesium sulfate. Concentration and silica gel chromatography (1:1 ethyl acetate:hexanes) afforded the title compound (42 g) as a pale yellow oil.

$^1$H NMR (CDCl₃) δ 1.3 (t, 3H), 2.6 (s, 3H), 2.65 (s, 3H), 2.8 (q, 2H), 3.6 (s, 2H), 3.75 (s, 3H), 5.45 (s, 2H), 6.9 (s, 1H), 7.1 (d, 2H), 7.2 (d, 2H).

Step 3A, methyl
1-[4'-(2"-ethyl-5",7"-dimethylimidazo[4,5-b]-pyridin-3-yl)methylphenyl]cyclopent-3-ene-1-carboxylate The product of Step 2A, above (42 g, 126 mmol), was dissolved in 620 ml anhydrous THF and 124 ml of 1,3-dimethyl-3,4,5,6-tetrahydro-2-(1H)-pyrimidinone (DMPU) and the solution was cooled to −78° C. and treated with potassium tert-butoxide (138.8 ml, 1M in THF, 138.8 mmol). After 15 minutes, cis-1,4-dichlorobut-2-ene (14.6 ml, 138.8 mmol) was added neat. The reaction mixture was then stirred at −78° C. for one hour and at −50° C. for another hour, then potassium tert-butoxide (138.8 ml, 1M in THF, 138.8 mmol) was added. After warming to room temperature the reaction mixture was heated to 50° C. for 1 hour and was then quenched with water. The THF was removed in vacuo and the residue was taken up in water and extracted with ethyl acetate. The combined organic layers were washed four times with saturated lithium chloride solution and dried over magnesium sulfate. Concentration and silica gel chromatography (3:1 hexanes:ethyl acetate) yielded the title compound (29 g) as a yellow oil.

$^1$H NMR (CDCl₃) δ 1.3 (t, 3H), 2.59 (s, 3H), 2.62 (s, 3H), 2.7 (d, 2H), 2.8 (q, 2H), 3.4 (d, 2H), 3.63 (s, 3H), 5.4 (s, 2H), 5.72 (s, 2H), 6.9 (s, 1H), 7.1 (d, 2H), 7.28 (d, 2H).

Step 4A,
1-[4'-(2"ethyl-5",7"-dimethylimidazo[4,5-b]-pyridin-3-yl)methylphenyl]cyclopent-3-ene-1-carboxylic acid A solution of the product of Step 3A, above (52 g, 134 mmol), and lithium hydroxide monohydrate (56.5 g) in 1350 ml of methanol and 1350 ml of water was heated to reflux for 3.5 hours. The reaction mixture was concentrated in vacuo to about one third of its original volume and the residue was washed with ether. The aqueous layer was adjusted to pH 4 with concentrated hydrochloric acid and acetic acid and was extracted three times with ethyl acetate-THF. The combined organic layers were washed with saturated sodium chloride solution and were dried over magnesium sulfate. Concentration afforded the title compound as a pale yellow solid which was purified as follows. The crude title compound (83 g) was suspended in 650 ml of ortho-dichlorobenzene and heated to reflux for 14 hours, then was allowed to cool slowly to room temperature over 6 hours. The precipitate that formed was filtered off and was washed with ethyl acetate. Two recrystallizations from ethyl acetate-THF afforded the purified title compound (45 g) as a colorless solid, mp 233°–234° C.

$^1$H NMR (DMSO-d$_6$) δ 1.24 (t, 3H), 2.5 (s, 6H), 2.6 (d, 2H), 2.8 (q, 2H), 3.3 (d, 2H), 5.4 (s, 2H), 5.75 (s, 2H), 6.95 (s, 1H), 7.09 (d, 2H), 7.3 (d, 2H).

I claim:

1. ($C_1$ to $C_4$ alkyl or halosubstituted $C_2$ to $C_4$ alkyl) 1-(4'-t-butyldimethylsilyloxymethylphenyl)cyclopent-3-ene-1-carboxylate.

2. The compound according to claim 1 which is methyl 1-(4'-t-butyldimethylsilyloxymethylphenyl)cyclopent-3-ene-1-carboxylate.

3. ($C_1$ to $C_4$ alkyl or halosubstituted $C_2$ to $C_4$ alkyl) 1-(4'-hydroxymethylphenyl)cyclopent-3-ene-1-carboxylate.

4. The compound according to claim 3 which is methyl 1-(4'-hydroxymethylphenyl)cyclopent-3-ene-1-carboxylate.

5. ($C_1$ to $C_4$ alkyl or halosubstituted $C_2$ to $C_4$ alkyl) 1-(4'-bromomethylphenyl)cyclopent-3-ene-1-carboxylate.

6. The compound according to claim 5 which is methyl 1-(4'-bromomethylphenyl)cyclopent-3-ene-1-carboxylate.

* * * * *